United States Patent
Dewey et al.

(10) Patent No.: US 8,475,507 B2
(45) Date of Patent: Jul. 2, 2013

(54) HANDHELD APPARATUS FOR USE BY A NON-PHYSICIAN CONSUMER TO FRACTIONALLY RESURFACE THE SKIN OF THE CONSUMER

(75) Inventors: David A. Dewey, Sunnyvale, CA (US); David M. Bradley, Redwood City, CA (US); Leonard C. DeBenedictis, Palo Alto, CA (US)

(73) Assignee: Solta Medical, Inc., Hayward, CA (US)

( * ) Notice: Subject to any disclaimer, the term of this patent is extended or adjusted under 35 U.S.C. 154(b) by 158 days.

(21) Appl. No.: 13/018,800

(22) Filed: Feb. 1, 2011

(65) Prior Publication Data

US 2012/0197357 A1   Aug. 2, 2012

(51) Int. Cl.
*A61N 5/06* (2006.01)

(52) U.S. Cl.
USPC .......................................................... 607/89

(58) Field of Classification Search
USPC ............. 607/88, 89, 90, 91, 92, 93, 94; 606/9
See application file for complete search history.

(56) References Cited

U.S. PATENT DOCUMENTS

| | | | |
|---|---|---|---|
| 5,558,666 A * | 9/1996 | Dewey et al. ..................... 606/9 |
| 5,599,636 A | 2/1997 | Braun | |
| 5,834,131 A | 11/1998 | Lutz et al. | |
| 6,002,240 A | 12/1999 | McMahan et al. | |
| 6,054,842 A | 4/2000 | Verzwyvelt et al. | |
| 6,676,655 B2 | 1/2004 | McDaniel | |
| 6,946,216 B2 | 9/2005 | Mu-Tsai et al. | |
| 7,118,563 B2 | 10/2006 | Weckwerth et al. | |
| 7,291,140 B2 | 11/2007 | MacFarland et al. | |
| 7,372,606 B2 | 5/2008 | Broome et al. | |
| 7,494,503 B2 | 2/2009 | McDaniel | |
| 7,824,395 B2 | 11/2010 | Chan et al. | |
| 7,938,821 B2 * | 5/2011 | Chan et al. ......................... 606/9 |
| 7,951,138 B2 * | 5/2011 | Whitaker et al. .................. 606/9 |
| 2004/0176754 A1 | 9/2004 | Island et al. | |
| 2006/0146384 A1* | 7/2006 | Schultz et al. ..................... 359/9 |
| 2006/0184214 A1 | 8/2006 | McDaniel | |
| 2007/0032847 A1 | 2/2007 | Weckwerth et al. | |
| 2007/0198004 A1 | 8/2007 | Altshuler et al. | |
| 2008/0015556 A1 | 1/2008 | Chan et al. | |
| 2008/0015557 A1 | 1/2008 | Chan et al. | |
| 2008/0058783 A1 | 3/2008 | Altshuler et al. | |
| 2008/0319430 A1 | 12/2008 | Zenzie et al. | |

(Continued)

FOREIGN PATENT DOCUMENTS

JP  10252467 A   9/1998
JP  2000323186 A  11/2000

*Primary Examiner* — Bill Thomson
*Assistant Examiner* — Sebastian X Lukjan
(74) *Attorney, Agent, or Firm* — Wood, Herron & Evans, LLP

(57) ABSTRACT

A handheld apparatus for delivering optical energy to fractionally resurface skin of a consumer is configured to be used by the non-physician consumer. The handheld apparatus includes a housing dimensioned for manual grasping and manipulation. The housing encloses a laser and an optical pattern generator having a rotatable component with a plurality of reflective segments that rotate through an optical beam from the laser to deflect and divide the optical beam into pulses that propagate from the housing and form a fractional pattern at the skin surface. The handheld apparatus also includes a transducer associated with fins on the rotatable component to generate signals for each pulse of electromagnetic radiation, the signals being monitored by a controller to enable an end of dose indication for the consumer when the treatment is completed.

19 Claims, 5 Drawing Sheets

U.S. PATENT DOCUMENTS

2009/0195848 A1 8/2009 DeBenedictis et al.
2010/0067081 A1 3/2010 Broome et al.
2010/0069898 A1 3/2010 O'Neil et al.
2010/0100159 A1 4/2010 Hamada et al.

* cited by examiner

HANDHELD APPARATUS FOR USE BY A NON-PHYSICIAN CONSUMER TO FRACTIONALLY RESURFACE THE SKIN OF THE CONSUMER

BACKGROUND

The invention relates generally to an apparatus for delivering optical energy and, in particular, to a handheld apparatus configured to conduct resurfacing or other cosmetic treatment of skin with optical energy.

Optical energy, particularly laser energy, is commonly used as a versatile tool in medicine to achieve desired outcomes in a tissue that is treated. For example, lasers and other forms of intense light have been used to treat common dermatological problems such as hypervascular lesions, pigmented lesions, acne scars, rosacea, and/or for hair removal. Forms of optical energy are also used for cosmetic purposes, to achieve a better cosmetic appearance by resurfacing the skin, by remodeling the different layers of skin to improve the appearance of wrinkled or aged skin, and/or by tightening the skin.

Generally, skin resurfacing is understood to be the process by which the top layers of the skin are completely removed using chemicals, mechanical abrasion or optical energy in order to promote the development of new, more youthful looking skin and stimulate the generation and growth of new skin. In laser skin remodeling, laser energy penetrates into at least a portion of the deeper layers of the skin and is aimed at stimulating the generation of and/or altering the structure of extra-cellular matrix materials, such as collagen, that contribute to the youthful appearance of skin.

During dermatological tissue treatment utilizing optical energy, a light beam irradiates the skin surface of a patient. Generally, lasers that are used for such treatment operate at a wavelength that is absorbed by one of the natural chromophores in the skin, such as water. If water is the primary chromophore, cellular and interstitial water absorbs light energy and transforms the light energy into thermal energy. The transport of thermal energy in tissues during treatment is a complex process involving conduction, convection, radiation, metabolism, evaporation and phase change that vary with the operational parameters of the light beam. These laser-based procedures should not damage the tissue underlying or surrounding the target tissue area.

The light beam optical operational parameters, such as wavelength, power, the intensity of the light, pulse duration, rate of emission, etc. may be selected to heat the cellular and interstitial water in a patient's skin, which causes temperature increases that produce a desired dermatological effect. Conversely, improper selection of the optical operational parameters can result in undertreatment or overtreatment of the tissue. Therefore, the optical operational parameters used in the treatment should be accurately controlled so that the light is delivered to the tissue with the proper fluence and in a uniform, controllable manner. A variety of devices have been proposed that intelligently control laser beam power, intensity, duration, etc. However, as will be discussed in greater detail below, application of these devices have significant disadvantages.

Known devices for dermatological tissue treatment include a hand-held delivery apparatus, sometimes referred to as a handpiece. A handpiece is the preferred means by which physicians apply treatment to tissue. During treatment, the handpiece emitting light is moved by a physician or health care professional's hand along the tissue to be treated. Treatment level from such a device is typically set in advance by manually selecting one or more light beam operational parameters. The operational parameters, which for example include power level, energy, pulsation rate, temperature, light intensity, current, etc., determine the degree of treatment of the entire treatment process.

One disadvantage of some of the existing handpiece apparatuses is that they require strict precision in positioning of the handpiece and application of controlled movement in order to stay within limits of uniform and efficacious treatment. Theoretically, strict precision can be achieved with a high degree of skill, attention and dexterity from the treating physician. In a real procedure, however, manual application and control of the handpiece can easily result in non-uniformity of treatment due to imprecise or involuntary movements of the human hand and/or uneven tissue surfaces. This often results in either some areas of the targeted tissue being under-treated, or causes some areas to be over-treated.

Consequently, a typical method of using conventional handpieces to deliver an optical energy based treatment is to produce a macroscopic, pulsed treatment beam that is manually moved from one area of the skin to another in a patchwork-like or stamping manner (i.e., the handpiece is not in continual motion when the treatment beam is applied) in order to treat a larger portion of tissue. Such an approach can have the disadvantage of producing artifacts and sharp boundaries associated with the inaccurate positioning of the individual treatments with respect to the treated skin surface.

Increasingly, conventional bulk skin treatment methods are being replaced by fractional treatment methods, as the use of fractional treatment methods has been found to produce fewer and less severe side effects than conventional bulk treatment methods, such as, for example, reduced damage to the epidermal layers of the skin. Fractional treatment methods involve the generation of a large number of relatively small treatment zones within a portion of tissue. The optical energy impacts directly on only the relatively small treatment zones, instead of impacting directly on the entire portion of tissue undergoing treatment, as it does in conventional bulk treatments. Thus, a portion of skin treated using a fractional optical energy treatment method is composed of a number of treatment zones where the tissue has been treated directly by the energy, contained within a volume of tissue that has not been treated directly by the energy. The treatment can, for example, produce coagulation and/or necrosis of tissue. Fractional treatment methods make it possible to leave substantial volumes of tissue untreated (e.g., uncoagulated and/or viable) within a portion of tissue that has been treated.

Devices which are capable of providing fractional treatments sometimes employ a stamping means as discussed above for delivering optical energy. Other devices employ means to scan one or more beams of optical energy across a portion of tissue, or a means to divide one or more beams of optical energy into a plurality of beams, and deliver the plurality of beams to a portion of tissue to be treated as the handpiece is moved. These additional scanning or dividing components are often located in the handpiece, making the handpieces for fractional scanning treatment devices more complex than the handpieces for bulk treatment devices and stamping treatment devices.

Complex handpieces, such as those that deliver uniform, controlled treatments while in motion can require the use of high manufacturing tolerances and/or the use of great precision when connecting the optical components of the handpiece as well as the rest of the device in order for the components of the device to function properly and for the device to deliver the optical energy in an efficient, effective, uniform, and controlled manner. For example, a large number of functional parameters need to be properly set in order for an optical energy system and/or source to function properly on its own. Similarly, a large number of functional parameters need to be properly set in order for a handpiece and its optical energy delivery system (e.g., scanner, lens array, or other means for delivering the treatment beam(s) to the portion of tissue) to function properly on their own, as well as to function properly in conjunction with an optical energy system and/or source. This inherent complexity has typically prevented such handpieces from being cost-effective to manufacture for home use by a non-physician consumer.

Therefore, an improved handpiece for dermatological treatment conducted by a non-physician consumer that addresses at least some of the shortcomings of conventional handpieces is desirable.

BRIEF SUMMARY

In general, the present invention is directed to a handheld apparatus for use by a non-physician consumer for fractionally resurfacing skin of a consumer. More particularly, the handheld apparatus applies optical energy to the skin of the consumer to cause regrowth and revitalization of the skin. The handheld apparatus is designed to be used by a non-physician consumer, such as in a home setting, and outside of the offices of a medical professional, a dermatologist, or other treatment specialist. The handheld apparatus addresses at least some of the problems encountered with prior art resurfacing devices as explained in detail above.

In one embodiment of the invention, the handheld apparatus includes a housing configured and dimensioned to be manually grasped and manipulated relative to a skin surface of the consumer. A laser, which is disposed inside the housing, is configured to generate an optical beam containing coherent electromagnetic radiation. The apparatus further includes an optical pattern generator inside the housing. The optical pattern generator includes a rotatable component configured to continually rotate about a rotation axis in a single direction and to deflect the optical beam during rotation to divide the electromagnetic radiation into pulses that propagate from the housing toward the skin surface and form a fractional pattern at the skin surface for performing a skin resurfacing dermatological treatment.

In another embodiment, the laser may be configured to generate the coherent electromagnetic radiation in the optical beam at a wavelength between 1.4 µm and 1.5 µm.

The optical pattern generator inside the housing may include a plurality of reflective axicon segments that rotate through the optical beam and optimally keep the beam focused at a constant point or position as each segment rotates through the beam. Alternatively, the optical pattern generator may include a spinning wheel with a plurality of deflection sectors, and each deflection sector including at least two reflective surfaces that deflect the optical beam in combination by a substantially constant angular deflection as the surfaces rotate through the beam. The handheld apparatus may further include a converging lens disposed in the path of the optical beam after deflection by the optical pattern generator. The converging lens is arranged to have a focal point above the skin surface so as to form a diverging optical beam at the skin surface, or alternatively may have a focal point on the skin surface or below the skin surface.

In one embodiment, the handheld apparatus further includes a plurality of rollers coupled with the housing. The rollers contact the skin surface as the housing is moved (or rolled over or across) and manipulated relative to the skin surface. The rollers effectively massage the skin surface to reduce pain sensations felt by a consumer during the skin resurfacing dermatological treatment. In this regard, an anesthetic is not required to be used with the handheld apparatus of the invention.

In another embodiment, the handheld apparatus also includes a fan which causes outside air to be blown through the housing so as to transfer heat away from the laser and keep its temperature within a predefined operating range and so that at least some of the heat is transferred to a rechargeable battery in the housing causing the battery to be heated and to increase a power output of the battery.

In a further embodiment, a controller is operatively coupled to an indicator and a transducer configured to output a signal for each pulse of the electromagnetic radiation generated by the optical pattern generator. The controller determines an accumulated number of pulses generated by counting each signal output by the transducer. The controller activates the indicator if the accumulated number of pulses exceeds a predetermined threshold number of pulses. To this end, the indicator produces a signal to the consumer that a desired radiation dosage has been delivered.

In yet another embodiment, the controller ensures that a fractional coverage of the skin surface with the electromagnetic radiation pulses is less than 80 pulses per square centimeter per pass. The controller also controls the spot size of each of the pulses at the skin surface to be between 30 micrometers and 300 micrometers in width. The controller maintains the energy of each of the pulses between 1 millijoule (mJ) and 20 mJ.

In yet a further embodiment, a lens is provided for focusing the optical beam, and the controller is programmed and the lens is configured and shaped to ensure that a fractional coverage is between 10 pulses/cm$^2$ per pass and 40 pulses/cm$^2$ per pass, a spot size of each of the pulses at the skin surface is between 80 µm and 200 µm, and an energy of each of the pulses is between 0.5 mJ and 10 mJ.

BRIEF DESCRIPTION OF THE SEVERAL VIEWS OF THE DRAWINGS

The accompanying drawings, which are incorporated in and constitute a part of this specification, illustrate various embodiments of the invention and, together with a general description of the invention given above and the detailed description of the embodiments given below, serve to explain the embodiments of the invention.

DETAILED DESCRIPTION

Generally, embodiments of the invention are directed to a handheld device for use by a non-physician consumer for fractionally resurfacing skin of the consumer during a skin resurfacing dermatological treatment. The handheld device, which is laser-based, may be used to rejuvenate the skin by producing thousands of tiny treatment zones in the skin, known as Microscopic Treatment Zones (MTZs), in a fractional pattern. When using the handheld device for a self-administered treatment, the non-physician consumer moves the tip of the handheld device over a treatment area. During the manual movement, laser pulses are fired onto the user's skin, creating the MTZ's. The MTZs may penetrate deep into the epidermis and may thermally damage old epidermal (e.g., pigmented) cells. During the motion over the treatment area, the handheld device treats only a fraction of any arbitrary region of the skin in the treatment area at a time, which leaves the surrounding skin area intact to promote fast healing. The speed of the tip with respect to the skin may be measured with an optical measurement system (i.e., a tracking system) and may be used as feedback in a closed control loop to control the laser firing rate. In this manner, a constant amount of energy per unit of skin area is deposited independent of hand speed variations during the manual movement. The natural healing mechanisms of the human body create new, healthy tissue that replaces skin imperfections and the healing is hastened by the presence of the intact skin surrounding the MTZs.

The treatment tip, which may have integrated rollers that contact the skin surface during treatment, is configured to be removed after each treatment for cleaning. The removable tip may also function as a key for the system to prevent unauthorized usage. The optional use of a pre-treatment optical tracking gel may help the optical speed measurement system to measure the speed in a reliable manner even in the absence of contrast on the skin.

The handheld device, which is cordless, includes a rechargeable battery that is recharged, when drained, by use of a power adapter and a base or charging unit. To that end, the handheld device may be docked in the charging unit, which is powered by the power adapter, and charged while located in the docked position. Optionally, the power adapter may also be directly connected to the handheld device, which permits the handheld device to be operated when the battery is drained.

Figure 1:
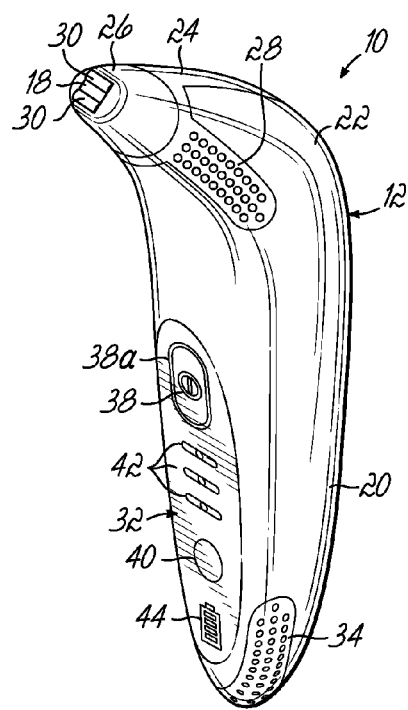
FIG. 1 is a perspective view of a handheld apparatus according to an embodiment of the invention.

With reference to FIG. 1 and in accordance with an embodiment of the invention, a handheld apparatus 10 for use by a non-physician consumer for fractionally resurfacing skin of the consumer is illustrated. The handheld apparatus 10 includes an outer casing or outer housing 12, an optical pattern generator 14 (not shown in FIG. 1) disposed inside the outer housing 12, and a laser 16 (not shown in FIG. 1) also disposed inside the outer housing 12. The laser 16 is configured to emit an optical beam containing coherent electromagnetic radiation for deflection by the optical pattern generator 14. The deflected optical beam may then be focused by one or more lenses before emission from the outer housing 12 at a light outlet 18. The handheld apparatus 10 is configured as a handpiece that can be manipulated relative to the skin surface of the consumer in a home setting by the consumer. To this end, the light outlet 18 may be moved across a portion of the skin surface to conduct a dermatological treatment on the skin surface such as skin tightening.

As explained in further detail below, the dermatological treatment may be a fractional resurfacing that produces thousands of microscopic treatment zones on the skin surface where old epidermal and dermal cells are damaged but left surrounded by untreated areas for rapid healing and production of new tissue. Preferably, the damaged or treated cells extend from an outer surface of the epidermis and into the dermis to form columns of damaged or treated cells, which are surrounded by columns of undamaged or untreated cells.

With reference to FIG. 1, the outer housing 12 includes a handle portion 20 and a tip portion 22 extending above the handle portion 20. The tip portion 22 is preferably generally angled from the handle portion 20 such that the handheld apparatus 10 has an ergonomic L-shaped contour for use by the consumer. The outer housing 12 is configured and dimensioned to be manually grasped and manipulated relative to the skin surface SS of the consumer. The outer housing 12 further includes a bezel or snout member 24 and a removable tip 26 which are each located at the tip portion 22. The snout member 24 sealingly couples to the outer housing 12 such that dust or other particulate matter is prohibited from entering the interior of the outer housing 12.

The snout member 24 has a plurality of inlet vent grills 28 projecting rearwardly from the removable tip 26 and towards the handle portion 20. The inlet vent grills 28 includes openings that serve as a cooling air inlet for air flow through the handheld apparatus 10, as further described with reference to FIG. 5 below. Alternatively, the inlet vent grills 28 may be formed on the outer housing 12 rather than on the snout member 24 in other embodiments. The handle portion 20 of the outer housing 12 includes at least one outlet vent grill 34 that serves as an outlet for air flow through the handheld apparatus 10 used as cooling air and to elevate the battery temperature, as further described with reference to FIG. 5 below.

The tip 26 is coupled to the snout member 24 in a frictional or snap fit. The tip 26 is generally formed from a translucent plastic material to permit more light to escape and reflect back into the outer housing 12, for purposes explained in further detail below. The tip 26 defines a truncated conical shape, with a pair of rollers 30 mounted at the free end away from the snout member 24. The pair of rollers 30 is configured to roll along the skin surface of a consumer during dermatological treatment. The pair of rollers 30 is mounted for free rotation on opposing sides of the light outlet 18, which is defined by the tip 26. The rollers 30 may be die cast or comprised of a rigid plastic material to enhance durability and to ease manufacturing.

The rollers 30 are configured to produce a massaging effect on the skin surface to reduce pain sensations otherwise caused by the light energy producing the microscopic treatment zones on the skin surface during the skin resurfacing dermatological treatment. Thus, a separate anesthetic is not necessary during use of the handheld apparatus 10 to perform the skin resurfacing dermatological treatment.

The handle portion 20 of the outer housing 12 includes a user interface panel 32 having a plurality of control buttons and indicator lights configured to enable user interaction with a controller 36 (shown schematically in FIGS. 2 and 6) for the handheld apparatus 10. In the illustrated embodiment, the user interface panel 32 includes a power button 38 at least partially backlit with a power button light emitting diode or LED indicator ring 38a, and an operational mode selection button 40. The power button 38 is configured to control the power supply of the handheld apparatus as well as communicate selected operational modes to the consumer, as explained in further detail below. The operational mode selection button 40 is configured to toggle the handheld apparatus 10 between one or more operational modes. In a preferred embodiment, three operational modes are provided: high intensity treatment, medium intensity treatment, and low intensity treatment, although the embodiments of the invention are not so limited. Each of these operational modes of the preferred embodiment is explained in further detail below.

The user interface panel 32 includes a plurality of, for example, three operational mode indicator lights 42 adjacent to the operational mode selection button 40 to identify which operational mode is active for the handheld apparatus 10. The user interface panel 32 further includes a battery indicator light 44 configured to identify the amount of charge remaining on an internal battery 46 (FIGS. 2 and 5) used as a power source to power apparatus 10 in a cordless manner. The battery 46 may be secured against movement by mounting in a battery cradle that is attached to the printed circuit board. In one representative embodiment, the battery 46 may be a lithium ion battery. It will be appreciated that each of the operational mode indicator lights 42 and the battery indicator light 44 may include one or more LEDs or similar light sources well known in the user interface panel art. The user interface panel 32 may also include a speaker 96 (see FIG. 2) configured to provide audible feedback to the consumer during use of the handheld apparatus 10. As examples, the speaker 96 may be used to audibly provide sound feedback to the non-physician consumer for a fault condition, an alert of overly-fast motion of the apparatus 10 relative to the consumer's skin surface SS, a ready-for-use prompt, and/or an end-of-dose notification.

Figure 2:
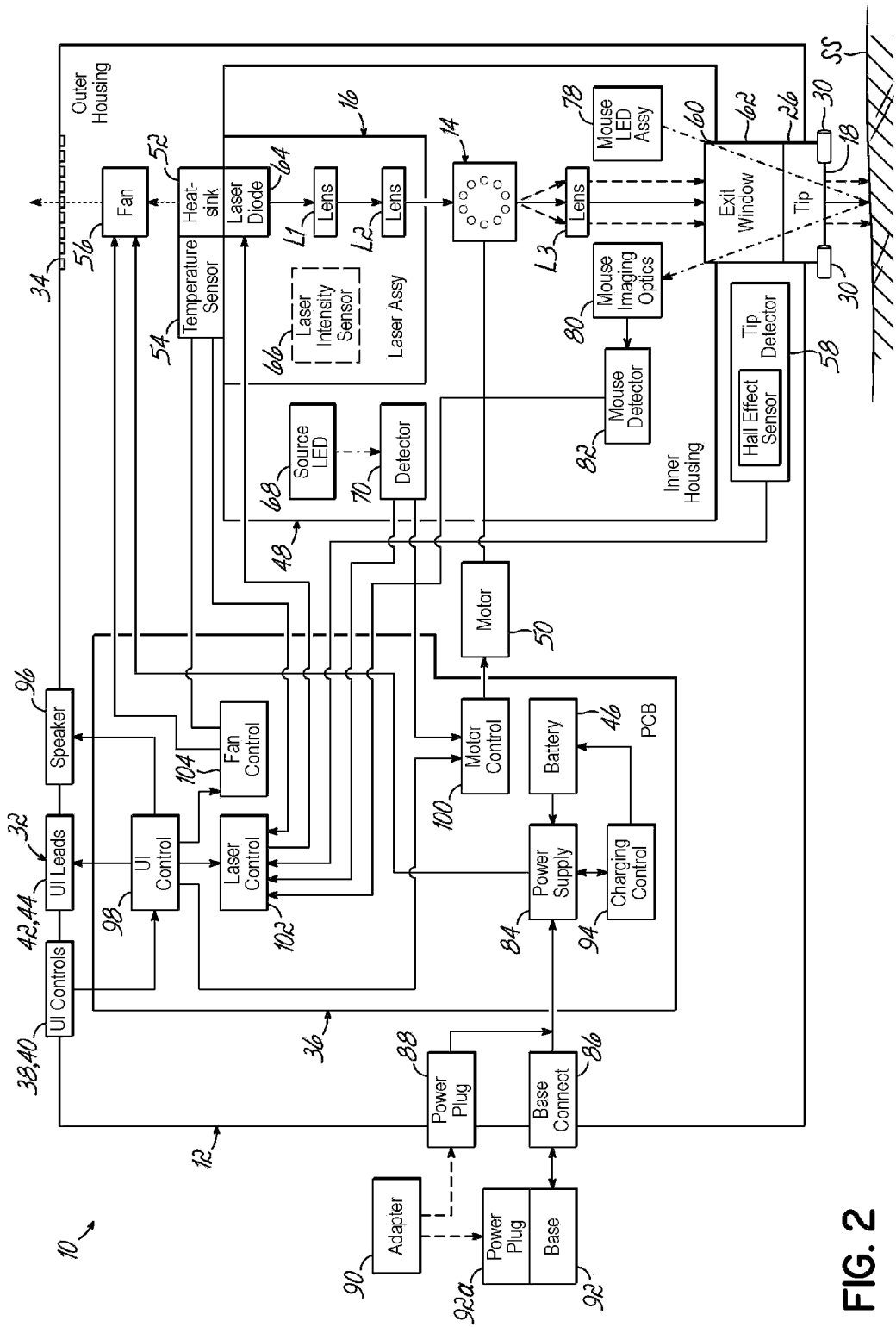
FIG. 2 is a schematic view of the handheld apparatus shown in FIG. 1.

With reference to FIG. 2, the structural and operational components of the handheld apparatus 10 are schematically illustrated. The outer housing 12 surrounds an inner housing 48 configured to contain optical components, a printed circuit board (PCB) populated with integrated circuits and other electronics components serving as the controller 36, and other non-optical components outside the inner housing 48. These other non-optical components include a motor 50 configured to rotate the optical pattern generator 14, a heat spreader or heat sink 52, a temperature sensor 54, a fan 56 configured to induce air flow through the outer housing 12 from an ingress at the inlet vent grills 28 to an egress at the outlet vent grill 34, and a tip detector 58 configured to detect whether the tip 26 is engaged with the outer housing 12.

Figure 3:
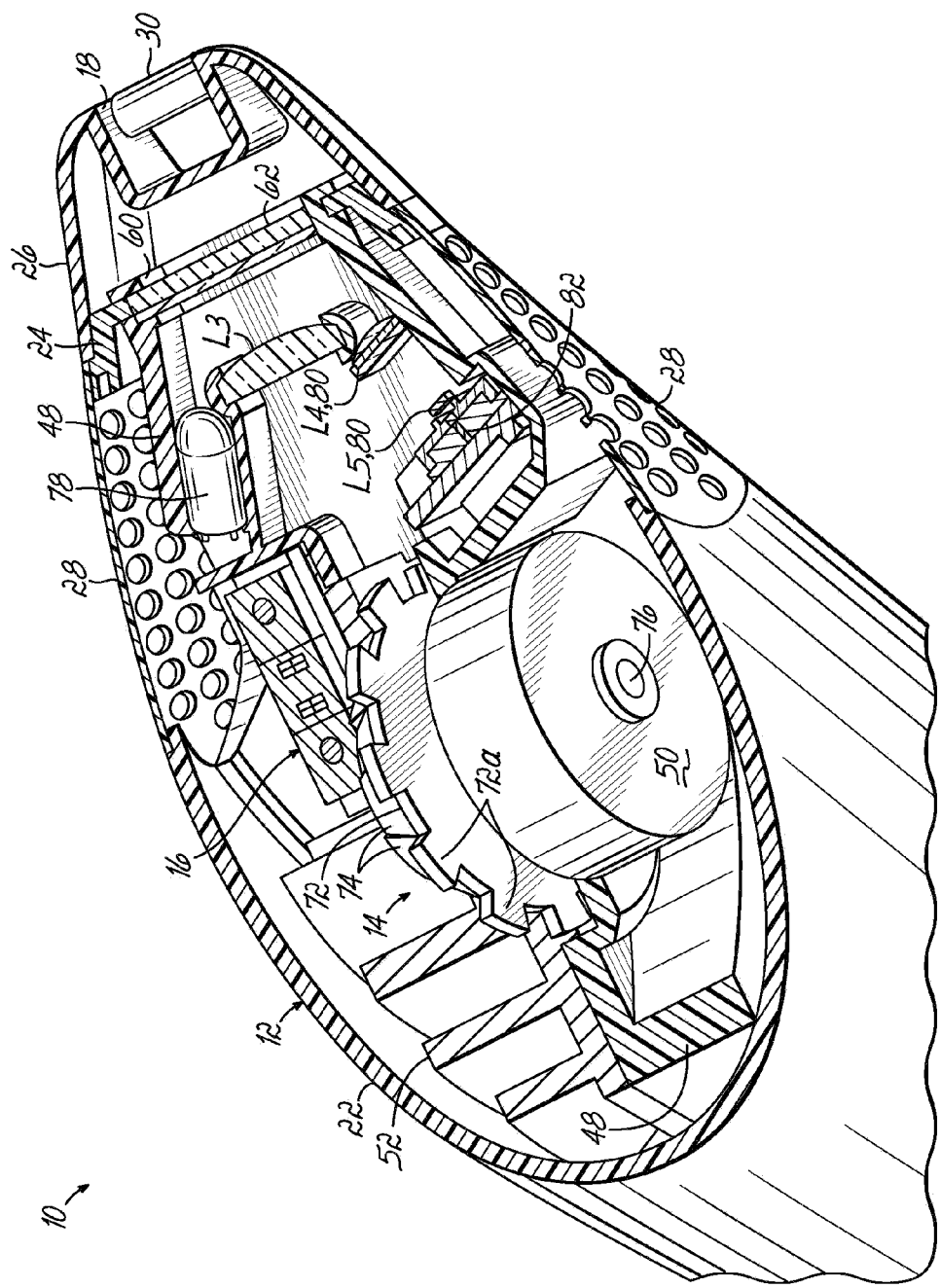
FIG. 3 is a partial cross-sectional view of a tip portion of the handheld apparatus shown in FIG. 1.

As shown schematically in FIG. 2 and in cross section in FIG. 3, the inner housing 48 nests within the tip portion 22 of the outer housing 12. The inner housing 48 may be composed of a lightweight plastic material and is configured to have a wall thickness, for example, of about 1.5 millimeters to 2.0 millimeters. The inner housing 48 includes an opening 60 directed towards the tip 26. This opening 60 is covered by an exit window 62 disposed in the snout member 24 when the snout member 24 is engaged, preferably sealingly, with the outer housing 12. The exit window 62 is sized to maximize the transmission of light energy between the inner housing 48 and the exterior environment (including a consumer's skin surface SS during treatment). In an alternative embodiment, the exit window 62 may be formed in the inner housing 48.

The laser 16 may be an assembly that includes a laser diode 64, a first lens L1, a second lens L2, and a laser intensity sensor 66. The laser diode 64 is configured to emit coherent electromagnetic energy (also referred to herein as light energy) at a given characteristic wavelength and with a line width centered about the given characteristic wavelength. The electromagnetic energy propagates as an optical beam along an optical axis through the first lens L1 and the second lens L2. For example, the laser diode 64 may generate a beam of coherent electromagnetic radiation in an optical beam preferably at a wavelength between 1.42 micrometers (μm) and 1.45 μm, a preferred wavelength being 1.435 μm. Other wavelengths can be used according to the embodiments of the invention; preferred ranges for the wavelength include 1.4 μm to 1.5 μm, 1.4 μm to 1.7 μm, 1.3 μm to 10.6 μm, and 1.3 μm to 20 μm.

In the representative embodiment, the laser diode 64 is a diode laser, but it will be appreciated that the laser 16 may include any suitable laser useful for dermatological treatment and capable of being packaged in a handheld device form factor. The first lens L1 collimates the electromagnetic energy along a fast axis, while the second lens L2 collimates the light energy along a slow axis. With the electromagnetic energy fully collimated into a focused optical beam, the pulse of light energy then exits the laser 16 at the second lens L2 and travels to the optical pattern generator 14.

The laser intensity sensor 66 monitors the energy level or intensity of the electromagnetic energy in the optical beam and is coupled in communication with the laser 16 and/or the controller 36. The laser diode 64 is configured to produce electromagnetic energy with multiple different energies or intensities that are selectable by the operator. In an exemplary operation, the laser diode 64 may be configured to produce electromagnetic energy having 3 millijoules (mJ) of energy in a low intensity treatment mode, 7 mJ of energy in a medium intensity treatment mode, and 9 mJ of energy in a high intensity treatment mode. The laser intensity sensor 66 can be used to monitor the energy level or intensity of the electromagnetic energy for comparison with the treatment mode that is selected.

As described above, the laser 16 generates an optical beam that propagates along an optical path toward the optical pattern generator 14. The laser 16 is not coupled with the optical pattern generator 14 by an optical fiber, but instead launches the optical beam into an air space across which the optical beam propagates to a rotatable component 72 of the optical pattern generator 14. In the embodiment illustrated in FIGS. 3 and 4, the optical pattern generator 14 is an axicon-type of optical pattern generator 14. An axicon-type of optical pattern generator 14 is disclosed in United States Patent Application 2009/0195848, published Aug. 6, 2009 and entitled "Optical Pattern Generators Using Axicon Segments", which is hereby incorporated by reference herein in its entirety.

Figure 4:
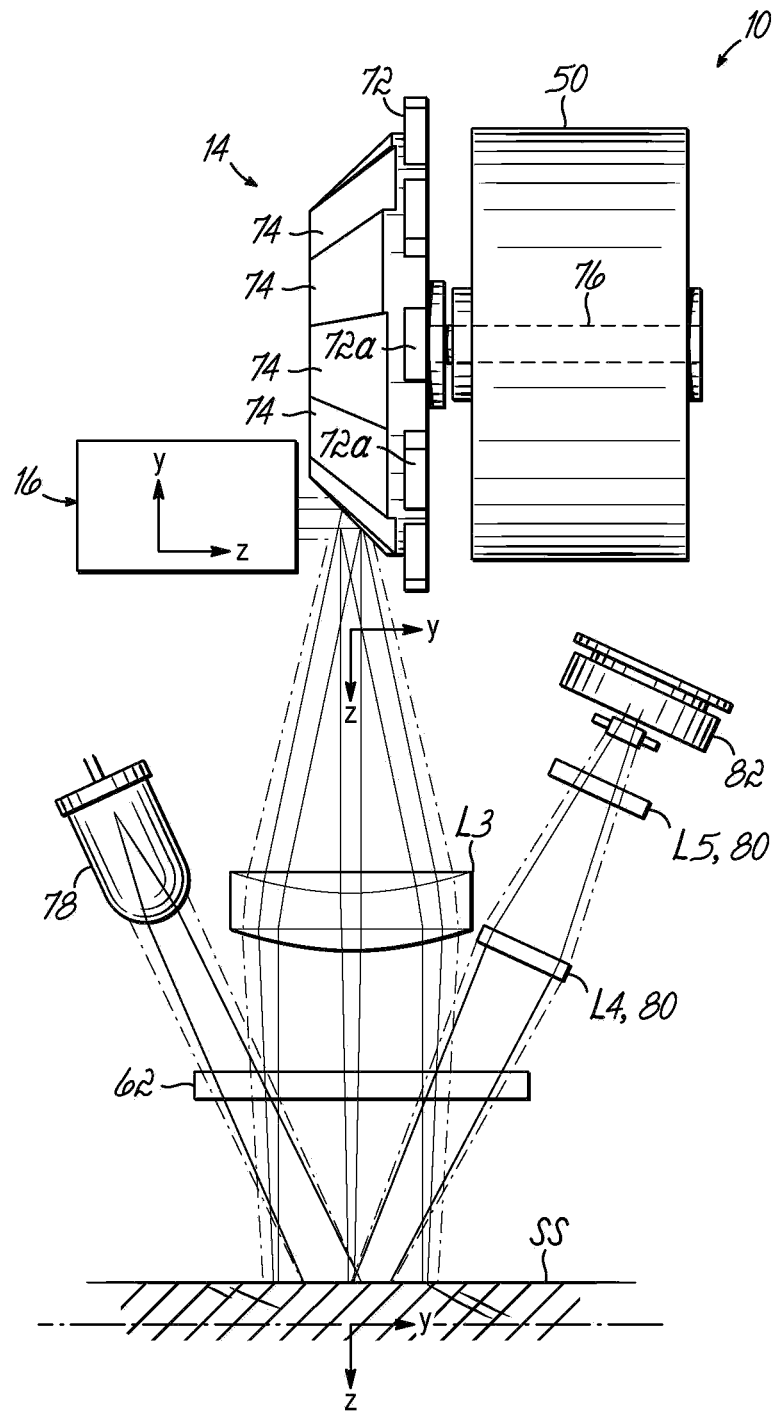
FIG. 4 is a schematic side view of various optical components of the handheld apparatus visible in FIG. 1.

As shown most clearly in FIG. 4, the optical pattern generator 14 may include the rotatable component 72 having a plurality of axicon segments 74 for deflecting the optical beam from the laser 16. The rotatable component 72 is coupled to the motor 50 by a drive shaft 76. The drive shaft 76 may be press fit into the rotatable component 72 in the exemplary embodiment. When driven by the motor 50, the rotatable component 72 is configured to continuously or continually rotate about a rotation axis (defined along drive shaft 76) in a single direction. As the rotatable component 72 continually rotates, the axicon segments 74 deflect the optical beam to divide the electromagnetic radiation in the optical beam into multiple rays or pulses of light energy, each having different angular deflections. The pulses of light energy propagate from the outer housing 12 toward the skin surface SS and form a fractional pattern at the skin surface SS for performing a dermatological treatment, such as a skin resurfacing dermatological treatment.

The speed of motor 50 may be monitored by an encoder/interruptor assembly that includes a source LED 68 and a detector 70 and that is coupled in communication with the controller 36. The rotatable component 72 may include a plurality of fins 72a corresponding to the number of axicon segments 74. The detector 70 is positioned such that each of the plurality of fins 72a on the rotatable component 72 blocks or interrupts the light originating at the source LED 68 from arriving at the detector 70 each time the corresponding axicon segment 74 begins to pass by the incoming optical beam. The detector 70 can therefore sense how fast the rotatable component 72 and the motor 50 are rotating and communicate an intermittent signal to the controller 36 with a periodicity that indicates motor speed. The detector 70 thus defines a transducer configured to output a signal for each pulse of the electromagnetic radiation generated by the rotatable component 72. The controller 36 is operatively coupled by the printed circuit board and/or wiring to the detector 70. In response to receiving the signals, the controller 36 is configured to determine an accumulated number of pulses by counting each arriving signal communicated from the detector 70, to compare the accumulated number of pulses with a threshold number of pulses, and to cause an indicator to activate if the accumulated number of pulses exceeds the threshold number of pulses signifying an end of dose. The controller 36 is also operative coupled to the indicator, which may be speaker 96 for producing an audible end of dose indication for the consumer or one of the indicator lights on the user interface panel 32 for producing a visual end of dose indication for the consumer.

The multiple pulses of light energy from the optical pattern generator 14 are imaged by a third lens L3 coupled to the inner housing 48 as shown in FIG. 3. The third lens L3 is disposed in the path of the optical beam after deflection as pulses by the optical pattern generator 14. The third lens L3 operates effectively as an aspheric lens with a focal point at the axicon segments 74 such that the multiple pulses of light energy coming into the third lens L3 at varying deflection angles exit the third lens L3 in generally parallel relation. These generally parallel pulses of light energy propagate through the exit window 62 and the light outlet 18 toward the skin surface SS and form a fractional pattern at the skin surface SS to perform a skin resurfacing dermatological treatment.

At least two of the axicon segments 74 have different included angles. Axicon segments 74 are surfaces of revolution. In one example, the axicon segments 74 are rotationally symmetric about an axis of revolution. In some embodiments, the axicon segments 74 are positioned so that their axes of revolution are coincident with the rotation axis for the rotatable component 72, and the optical beam travels to the axicon scanner along a direction parallel to this rotation axis. In this way, the shape presented by an axicon segment 74 to the incoming optical beam does not change as the axicon segment 74 rotates through the incoming optical beam and the corresponding divided pulses of light energy produced will also not change. Alternatively, the rotation axis of the rotatable component 72 may be parallel to, but displaced from, the axes of revolution of the individual axicon segments 74. This arrangement can be used to create divided pulses of light energy that move slightly for each individual axicon segment 74. According to a preferred embodiment, a width of a treatment zone on the skin surface spanned by all the segments can be approximately 10 mm, though other widths are envisioned, such as a width between 2 mm and 30 mm, 4 mm and 20 mm, 5 mm and 15 mm, 7 mm and 13 mm, and 8 mm and 10 mm.

In one embodiment, the optical pattern generator 14 may include eleven axicon segments 74. It will be understood that the optical pattern generator 14 may be modified in alternative embodiments to provide differing fractional patterns for dermatological treatment. For example, in another embodiment, the number of axicon segments 74 on the rotatable component 72 may be increased to twenty-nine. The number of axicon segments 74 may be any number, but having an odd number or a prime number of axicon segments 74 is desirable because the randomness of fractional pattern is improved with odd numbers or prime numbers of axicon segments 74.

Alternatively, the optical pattern generator 14 may include other types of reflective facets instead of axicon segments 74. In one example, each reflective facet is configured to deflect and divide the incoming optical beam at varying angles. Similar to the previously-described axicon segments 74, the number of reflective facets in such an embodiment should also be an odd number or a prime number to increase randomness of the fractional pattern of light energy produced for each actuation of the laser 16. The controller 36 may be configured to actuate the laser 16 such that all reflective facets are never sequentially continually illuminated, thereby reducing the possibility of a repeating fractional pattern generated by the optical pattern generator 14.

In another example, each reflective facet of the optical pattern generator 14 includes a deflection sector having at least two reflective surfaces that in combination deflect the incoming optical beam by a substantially constant angular deflection as the deflection sector rotates through the incoming optical beam. Such an optical pattern generator 14 is disclosed in United States Patent Application 2010/0067081, published 20100067081 and entitled 'Optical Pattern Generator Using a Single Rotating Component", which is hereby incorporated by reference herein in its entirety. Although each deflection sector deflects the incoming optical beam by a substantially constant angular deflection, the deflection sectors may be configured such that each deflection sector has a different constant angular deflection of the incoming optical beam. The deflection sectors permit the fractional pattern generated by the optical pattern generator 14 to be independent of the wavelength of the incoming optical beam.

Although the third lens L3 is illustrated as an aspheric lens schematically in FIGS. 2 and 4, the third lens L3 may also be a converging lens that tends to deflect the various pulses of light energy toward a focal point downstream of the converging lens. The converging lens L3 may be positioned such that the focal point is located above the skin surface SS, and more particularly, inside the outer housing 12. To this end, the various pulses of light energy come together at the focal point within the outer housing 12 and then diverge to form the fractional pattern on the skin surface SS for dermatological treatment. It will be understood that the converging lens may include a simple lens, or the converging lens may be a portion of a compound lens. Alternatively, the focal point for the third lens L3 may be on the skin surface SS or below the skin surface SS.

Consequently, the optical components (laser 16, optical pattern generator 14, and third lens L3) cooperate to treat the skin surface SS with a randomized fractional pattern of laser light energy.

The controller 36 is configured to prevent activation of the laser 16 unless the tip 26 is properly coupled to the outer housing 12. The controller 36 is coupled in communication with the tip detector 58 that aids in ensuring proper operation of the handheld apparatus 10. In this regard, the tip detector 58 may include a Hall effect sensor and the tip 26 may include a magnetic element (not shown). The Hall effect sensor is sensitive to changes in the local magnetic field. When the magnetic element of the tip 26 comes into close proximity to the tip detector 58, the tip detector 58 generates a signal that the tip 26 is properly engaged and the signal is communicated to the controller 36. If the tip 26 is properly coupled to the outer housing 12, the controller 36 responds to the signal from the tip detector 58 by permitting the laser 16 to be activated.

The controller 36 is also configured to prevent the laser 16 from actuating if the handheld apparatus 10 is not being moved by the consumer at an appropriate velocity relative to the consumer's skin surface SS during treatment. For effective dermatological treatment, a roughly consistent desired dosage per square centimeter of skin surface SS should be maintained throughout the treatment of an area. Assuming the laser 16 actuates at predetermined intervals of time, the dosage of the treatment varies inversely to variations in the consumer's hand speed in moving the handheld apparatus 10. To this end, when the velocity of the optical beam relative to the target area increases during treatment, the dosage of the delivered treatment decreases, and vice versa. Thus, the usual imprecision of manual movement of the handheld apparatus 10 can result in non-uniformity. If the consumer moves the handheld apparatus 10 too quickly, the dosage of the treatment applied will not be sufficient to achieve desirable skin resurfacing results. If the consumer moves the handheld apparatus 10 too slowly or not at all, the dosage of the treatment should be limited. Thus, it is desirable to compensate the control of the laser 16 for the various application velocities, as long as the velocity of the handheld apparatus 10 stays within a desired range (determined by treatment effectiveness). To this end, the movement and/or velocity of the handheld apparatus 10 may be detected.

The representative embodiment of the handheld apparatus 10 therefore includes a movement/velocity detection system, which comprises a mouse LED assembly 78, mouse imaging optics 80, and a mouse detector 82, coupled in communication with the controller 36. As the element names indicate, the movement/velocity detection system operates in a similar manner as an optical mouse for a personal computer. As shown more clearly in FIG. 3, the mouse LED assembly 78 is positioned adjacent to the third lens L3 and close to the exit window 62 so that a substantial portion of light emitted from the mouse LED assembly 78 is delivered to the skin surface SS. The emitted light is scattered from the skin surface SS, and a portion is reflected back through the generally translucent tip 26 and exit window 62. The mouse imaging optics 80 includes a fourth lens L4 and a fifth lens L5 (see FIG. 4) placed in the optical path from the skin surface SS to the mouse detector 82 so as to image the skin surface SS on the mouse detector 82. The mouse detector 82 is configured to only detect reflected light from the mouse LED assembly 78 so that the optical beam treating the skin surface SS does not interfere with position and velocity detection.

Other configurations will be evident to those skilled in the art, including the use of a CCD camera, or an optical sensor array instead of the mouse detector 82. An advantage of the movement/velocity detection system is that if the handheld device 10 is not in contact with the skin surface, a velocity will not be detected (since the skin will be out of focus) and the laser will thus not fire since a minimum velocity will not be detected. Also, as previously mentioned, preferably a wavelength such as 1.42 μm to 1.45 μm can be used.

The mouse detector 82 determines the position and velocity of the handheld apparatus 10 at the tip 26 by continuously scanning and comparing reflected light from the mouse LED assembly 78 and the skin surface SS. The mouse detector 82 then provides this information to the controller 36, which determines whether the velocity is within the desired range for treatment. Furthermore, the controller 36 may modify the speed at which the laser 16 actuates depending on this detected velocity, as described in further detail below.

The detection of velocity by the mouse detector 82 can be improved or made more robust by the addition of a substance to the skin surface SS, the substance (e.g., an optical tracking gel) having the effect of enhancing the contrast for the mouse detector 82. Such a contrast enhancing substance may include, for example, particles, suspensions, colloids, emulsions or solutions. One example of particles that may be used as a contrast enhancing substance would be ink particles that are spread onto the skin by painting or marking the skin prior to treatment with the handheld apparatus 10. Particles such as carbon particles or fluorescent particles may be used in some embodiments. As a further example, OptiGuide Blue dye produced by Reliant Technologies, Inc. of Hayward, Calif., may be used as the contrast enhancing substance. Contrast enhancing substances are not being used in this context solely or even primarily as absorbing targets or chromophores for a treatment or diagnostic wavelength, nor are they solely or primarily used as a means to show what areas have already been treated. Contrast enhancing substances may be effective due to their absorption or reflection of light. Skin is generally reflective for visible light wavelengths, so a contrast enhancing substance that is highly absorptive for the illuminating wavelength will be easily detectable. Alternately, using a contrast enhancing substance that is more reflective than skin for the illuminating wavelength will also improve the detectability.

The use of contrast enhancing substances, such as dyes, inks, particles, solutions, etc. that do not absorb the treatment wavelength, but which enhance the contrast of the viewing of the treatment surface by the mouse detector 82, allows the detection to have high signal-to-noise ratio (SNR) and subsequently good surface quality (SQUAL) values, which in turn improves the reliability of the treatment. Different dyes have different visual effects. For example, a dye including cyan blue (FD&C Blue #1) may look rather unnatural to patients and sometimes may cause post treatment staining of certain skin types, resulting in more post treatment cleaning than may be desirable. It should be noted that darker skin types have higher SQUAL values than lighter skin types using a red LED (610 nm-650 nm), due to the presence of easily detected patterns of melanin in darker skin.

The contrast enhancing substance may be chosen based in part on skin tone and the wavelength of light used by the detection system. Thus, an orange-red LED in the mouse LED assembly 78 may be enhanced in its detection sensitivity by applying blue or black dye, ink or particles to the tissue surface. The blue dye may have some disadvantages as described above. However, by adding subtractive red and yellow dyes to a bright blue dye, the result is a brown dye that is less distracting to view, and, when removed after treatment, does not need to be removed completely for the patient to appear to have a relatively normal skin tone. In fact, proper design of the dye allows either no residue, similar residue ratio of the original dye mixture, red residue that blends in with the erythema post-treatment, or even a slight green residue to help cover the erythema caused by the treatment and to act as a cosmetic post-treatment cover up. The addition of the reds and yellows does not impair the performance of the mouse detector 82, since the contrast is determined primarily by the blue dye concentration and by the variations of the dye thickness as it accumulates in dermatoglyphic folds in the skin or is purposely applied with an applicator that creates a speckled pattern for the detector to identify for purposes of focus detection and velocity or position detection. In other words, viewed in the light of the mouse LED assembly 78, the appearance of the skin is the same as whether with the pure blue dye or with the brown dye. Dyes such as the following examples have been used to formulate the brown dye: FD&C Blue #1, FD&C Red #40, FD&C Yellow #5, FD&C Yellow #6, D&C Red #22, and D&C Red #33.

In embodiments using contrast enhancing substances such as dyes, ink solutions, or suspensions, application of the contrast enhancing substance may be achieved simply by applying the substance onto the skin with a cotton swab or other applicator. The substance should typically be evenly spread out and left to dry, although being evenly spread out or allowed to dry are not required in all cases. This process uses the natural skin irregularities and folds where the substance infiltrates or accumulates to enhance the contrast for imaging. Typically, a thicker layer of substance remains within skin folds, while in general less substance stays on flatter potions of the skin. The substance stains may appear random, patchy, and irregular, enhancing the natural features and the observed contrast of the skin to be imaged. Relative position and velocity values can be extracted based on this simple process. The technique does not require placement of regular patterns or graphics on the skin to be useful.

The controller 36 is also configured to prevent the laser 16 from actuating if the temperature of either the laser 16 or the outer housing 12 reaches intolerable levels. More specifically, the controller 36 is configured to power down the handheld apparatus 10 when the laser 16 or the outer housing 12 exceeds a threshold temperature (e.g., 43° C.) so that the laser 16 and the consumer are each protected from intolerably high operating temperatures. The temperature sensor 54 within the outer housing 12 detects the local temperature adjacent to the laser 16 and communicates temperature readings as signals to the controller 36. In one embodiment, the temperature sensor 54 may be configured to sense the contact temperature of the heat sink 52.

The heat sink 52 is attached to the laser 16, as shown in FIG. 3, in a conventional manner and optionally with the presence of a thermal interface material so that heat is efficiently extracted from the laser 16, when the laser 16 is powered and generating heat. The heat sink 52 is machined or otherwise formed with a plurality of fins for transferring heat rapidly to flowing air, as is well understood, and a saddle to which the laser 16 is mounted. The heat sink 52 extracts heat from the laser 16 and dissipates the heat by transfer from the fins to the air flow. In a representative embodiment, the fan 56 may be a 35-millimeter blower that draws air directly through the inlet vent grills 28 and across the heat sink 52. The flow pathways (FP) of air traveling through the handheld apparatus 10 are further diagrammatically illustrated in FIG. 5.

Figure 5:
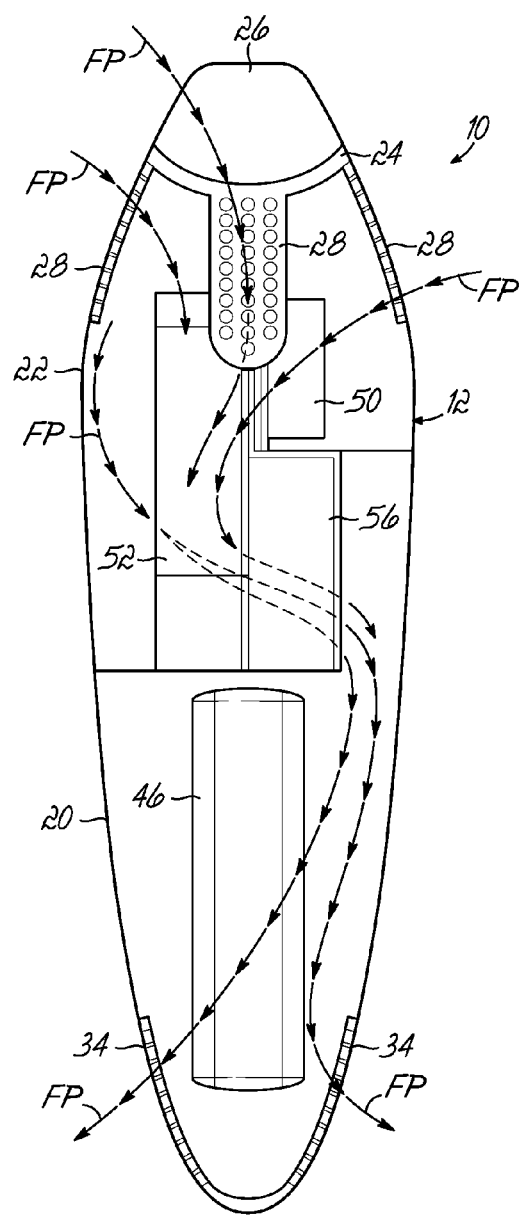
FIG. 5 is a schematic side view of the handheld apparatus shown in FIG. 1, illustrating air flow through the handheld apparatus.

Air that is circulated through the outer housing 12 by the fan 56 is used to maintain the temperature of the laser 16 below the specified threshold temperature. The outer housing 12 and the fan 56 are constructed and configured to cause outside air to be blown through the outer housing 12 and transfer heat away from the laser 16 so that at least some of the heat is transferred to the internal battery 46 causing the internal battery 46 to be heated. As shown in FIG. 5, the heated air that is blown from the fan 56 then travels through the handle portion 20 and generally around the internal battery 46 before exiting at the outlet vent grill 34. The air entering the outer housing 12 through the inlet vent grills 28 is at a lower temperature than the air heated by interaction with the heat sink 52 and discharged through the outlet vent grill 34. The walls inside the outer housing 12 may include baffles that assist in routing the air flow across the battery 46. Consequently, the internal battery 46 is heated by the air flow through the handheld apparatus 10.

As is well understood in the battery art, a small increase in battery operating temperature can improve the power output of the internal battery 46 at the expense of battery longevity. However, the battery life losses are minimal in the handheld apparatus 10, and the internal battery 46 is configured as a rechargeable battery in any event. Consequently, the induced air flow from the fan 56 provides multiple benefits for the handheld apparatus 10.

The handheld apparatus 10 may further include vibration isolator members (not shown) configured to dampen any undesirable vibrations that may be imparted to the laser 16 or other components. For example, the vibration isolator members may include small rubber cylinders mounted between the inner housing 48 and the outer housing 12 at various locations throughout the inner housing 48. The rubber cylinders deflect to absorb a substantial amount of vibrational shock, which protects the laser 16 from damage or improper operation. It will be understood that other types of known vibration isolator members may be used in alternative embodiments.

As shown schematically in FIG. 2, a power supply 84 on the printed circuit board is configured with circuitry to deliver power at proper voltage(s) to all of the powered components of the handheld apparatus 10 via respective controls described in further detail below. The power supply 84 may be configured to be coupled by an electrical interface of a base connect 86 with a charging/storage base 92. The base connect 86 may include a pair of charging pins interfaced with the printed circuit board and accessible from the exterior of the outer housing 12. Circuit paths on the printed circuit board couple the charging pins of the base connect 86 with the power supply 84. The charging/storage base 92 includes complementary charging pins positioned and configured to engage the pair of charging pins of the base connect 86 during storage between uses and recharging of the handheld apparatus 10.

A power adapter 90 is configured with circuitry to convert a source of electrical power (e.g., a wall outlet supplying conventional household alternating current (AC) power at 50 Hz or 60 Hz) to direct current (DC) power. The power adapter 90 is connected with a power plug 92*a* of the charging/storage base 92, which is configured to mechanically hold the handheld apparatus 10 during a charging cycle and for storage. Alternatively, the power adapter 90 may be directly connected with a power plug 88 disposed, for example, at the handle portion 20 of the outer housing 12 so that DC power can be delivered to the power supply 84 when the handheld apparatus 10 is not docked with the charging/storage base 92.

Also as shown in FIG. 2, the controller 36 includes a charging control 94 configured to supply power from the power supply 84 to the internal rechargeable battery 46 during a recharging cycle. Charging may be automatically initiated when the apparatus 10 is docked with the charging/storage base 92, provided the power adapter 90 is attached and plugged into the source of electrical power. When the handheld apparatus 10 is not connected to a source of power via the power plug 88 or the base connect 86, the power supply 84 receives power from the battery 46 and delivers that power at the proper voltage(s) to the various other controls described in further detail below.

The battery capacity of battery 46 is sufficient to provide uninterrupted electrical power for a specified period of time to the laser 16, the controller 36, the motor 50, the operational mode indicator lights 42, the battery indicator light 44, the temperature sensor 54, the fan 56, the laser intensity sensor 66, the source LED 68, the mouse LED assembly 78, the mouse detector 82, the tip detector 58, the user interface speaker 96, and any other component that requires electrical power in the handheld apparatus 10. The time period may be the maximum length of at least one dermatological treatment according a specified treatment protocol. For example, the specified period of time may be at least 40 minutes. Thus, the handheld apparatus 10 is configured to operate cordlessly throughout an entire treatment session without a direct corded, connection to an external power source and without being recharged. Other preferred uninterrupted electrical power periods can include anything over 10 minutes, 15 minutes, 20 minutes, 30 minutes, 40 minutes, 50 minutes, or 60 minutes, or even longer time periods.

Also shown in FIG. 2, the controller 36 includes a user interface control 98 configured to communicate with the components of the user interface panel 32. The user interface control 98 receives signals from UI controls including the power button 38 and the operational mode selection button 40. The user interface control 98 sends signals to actuate the various LEDs in the user interface panel 32 including the operational mode indicator lights 42 and the battery indicator light 44 (referred to collectively as UI leads in FIG. 2). The user interface control 98 also sends sound signals to operate the speaker 96 to provide audible feedback and/or instructions to the consumer.

The controller 36 also includes a motor control 100, a laser control 102, and a fan control 104 each in operative communication with the user interface control 98. Each of these controls 100, 102, 104 may be implemented by the controller 36 in software and/or hardware.

The motor control 100, based at least in part upon input from the user interface control 98, supplies a motor speed setpoint associated with the selected operational mode to the motor 50. In response, the motor 50 continuously spins or rotates the rotatable component 72 at a predetermined speed or angular velocity (e.g., desired speed) nominally equal to the motor speed setpoint. The motor control 100 is coupled in communication with the detector 70 of the encoder/interruptor and receives feedback on the motor speed, which is used to ensure that the rotatable component 72 is rotating at the desired speed. The measured motor speed from the detector 70 is compared by the motion control 100 with the motor speed setpoint to detect and correct deviations.

The laser control 102, based at least in part upon input from the user interface control 98, activates the laser 16 to supply an optical beam to the optical pattern generator 14 when the apparatus 10 is operating in compliance with the selected operational mode. Typically, the control 102 switches the laser 16 between a powered state in which light is emitted and an unpowered state in which light emission is absent. The laser control 102 may comprises a laser diode driver in the form of a constant current source that delivers exactly the current to the laser diode 64 that it needs to operate to provide the fractional skin resurfacing as described herein. The laser control 102 is also operatively connected to the temperature sensor 54, which measures the temperature of the laser diode 64 and provides temperature readings to the laser control 102 for use in temperature control. The laser control 102 is further operatively connected with the tip detector 58, the detector 70 of the encoder/interruptor, and the mouse detector 82 of the movement/velocity detection system.

The fan control 104 receives temperature readings from the temperature sensor 54 and controls the operation of the fan 56. The fan control 104 may also signal the user interface control 98 if the system temperature has exceeded a tolerable value (e.g., 43° C. in a representative embodiment).

Figure 6:
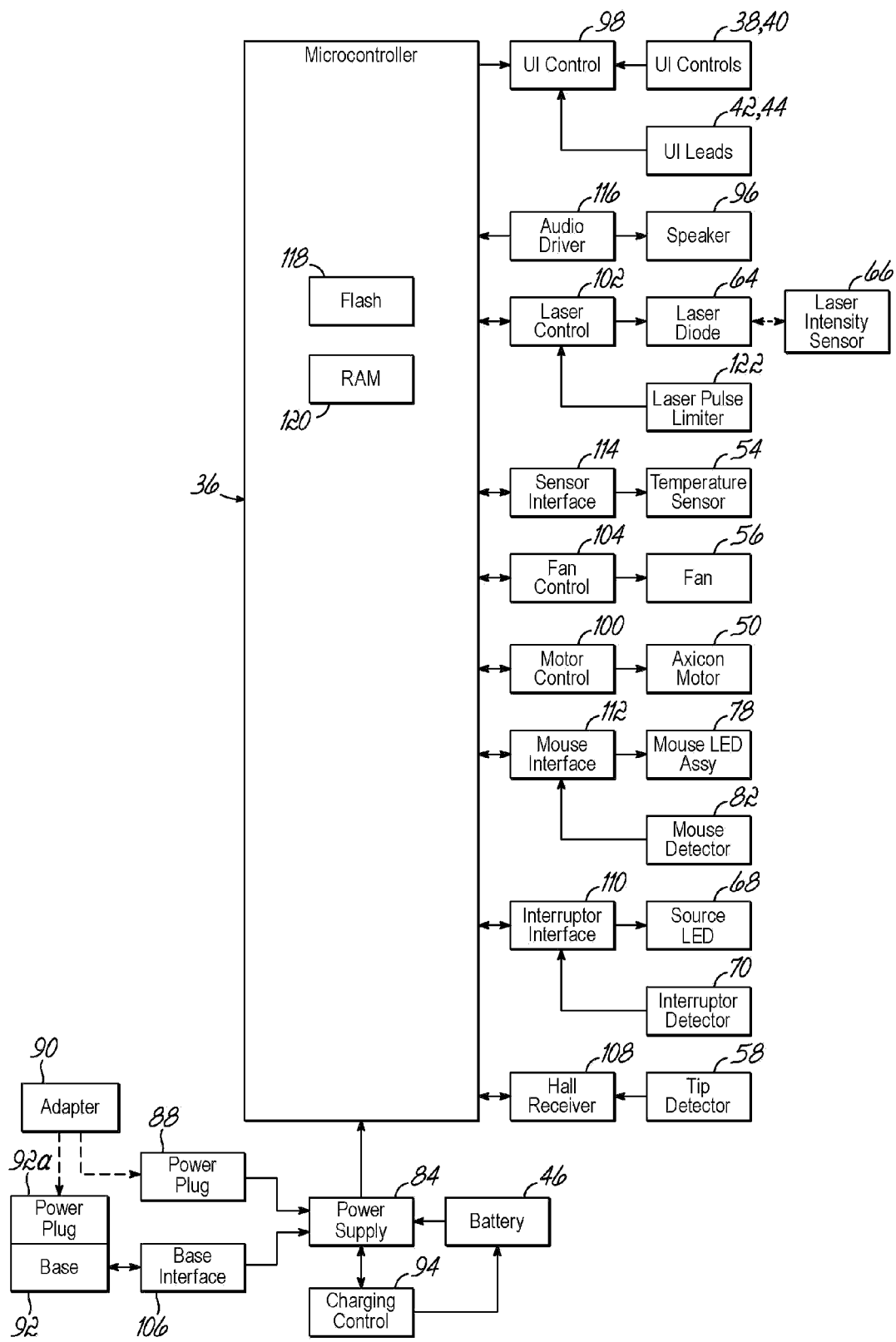
FIG. 6 is a schematic representation of the controller and associated components of the handheld apparatus shown in FIG. 1.

FIG. 6 further illustrates the electrical block diagram illustrating all electronic components of the handheld apparatus 10 and all operative connections associated with the controller 36. The controller 36 is configured to adjust in real-time the operational parameters of the laser 16 in response to detected variations in apparatus positional parameters, laser temperature parameters, and other parameters. Controller 36 may connected to an interface unit having a plurality of interface, control, and driver elements as shown in FIG. 6.

More particularly, the "interface unit" includes a base interface 106 communicating with the charging/storage base 92, the power supply 84, a Hall receiver 108 communicating with the tip detector 58, an interruptor interface 110 communicating with the encoder/interruptor, a mouse interface 112 communicating with the movement/velocity detection system, the motor control 100, the fan control 104, a sensor interface 114 communicating with the temperature sensor 54, the laser control 102, an audio driver 116 communicating with the speaker 96, and the user interface control 98. In sum, the interface unit receives signals from each of the electronic components, analyzes those signals for communication to the controller 36, receives programming logic instructions from the controller 36, and sends signals to actuate the various electronic components. It will be understood that the various interfaces, drivers, and controls making up the interface unit may include analog processing circuitry for normalization or amplification of signals as well as analog-to-digital converters or digital-to-analog converts as necessary for complete communication and control of the handheld apparatus 10.

The controller 36 can be implemented using at least one processor selected from microprocessors, micro-controllers, microcomputers, digital signal processors, central processing units, field programmable gate arrays, programmable logic devices, state machines, logic circuits, analog circuits, digital circuits, and/or any other devices that manipulate signals (analog and/or digital) based on operational instructions that are stored in a memory. The memory may be a single memory device or a plurality of memory devices including but not limited to random access memory (RAM), volatile memory, non-volatile memory, static random access memory (SRAM), dynamic random access memory (DRAM), flash memory, cache memory, and/or any other device capable of storing digital information. In a representative embodiment, the memory may comprise a flash memory 118 and a random-access memory (RAM) 120 shown schematically in FIG. 6.

The processor of the controller 36 operate under the control of an operating system, and executes or otherwise relies upon computer program code embodied in various computer software applications, components, programs, objects, modules, data structures, etc. The computer program code also includes a control algorithm that, when executing on the processor, controls and manages the operation of the apparatus 10 by using numerical calculations and operational logic in an appropriate control scheme. The computer program code typically comprises one or more instructions that are resident at various times in memory 120, and that, when read and executed by the processor of the controller 36, causes the apparatus 10 to perform the steps necessary to execute steps or elements embodying the various embodiments and aspects of the invention. In particular, the computer program code may include an algorithm that, when executing on the processer of the controller 36, ensures homogeneous intensity distribution of the treatment radiation across the treatment area and compensates for motion variations.

The controller 36 may determine a set of desired operational parameters (i.e., how the laser 16 and user interface panel 32 should be controlled to provide treatment and feedback to a consumer) in response to signals received from the interface unit. Based upon consumer input at the interface unit, the controller 36 determines a corresponding set of operational parameters. For example, the controller 36 can change operational parameters such as the speed of the motor 50 and the firing speed of the laser 16 in response to changes of detected velocity of the handheld apparatus 10 or in response to input at the operational mode selection button 40 of the user interface panel 32.

The controller 36 may calculate specific operational parameters, or may be logic based for systematically arriving at optimal operational parameters for the desired treatment using a software algorithm, as described in further detail below. The memories 118, 120 may store one or more look-up tables that are accessible for generating operational parameter values for the selected treatment based on measured velocity of the tip 26 and the selected operational mode (e.g., high intensity, medium intensity, or low intensity). Such memory-based look-up tables would provide coherent data sets of operational parameters associated with various corresponding values of velocity and operational mode. The applicable operational parameters would then be sent via the interface unit to control the operation of the various components of the handheld apparatus 10. Consequently, the controller 36 adjusts the operation of the handheld apparatus 10 in real time throughout the course of a dermatological treatment in response to, for example, motion (e.g., velocity) variations.

In operation, initial operational parameters are defined depending upon the selected operational mode input at the user interface panel 32. The operational parameters of the laser 16 that may be controlled are the energy of the optical beam and/or the treatment density, defined as the number of microscopic treatment zones (MTZ) per square centimeter per treatment pass of the handpiece. Given the laser power at the skin surface SS, a required pulse duration for the laser 16 to reach a desired level for the energy of the optical beam is calculated by the controller 36, as well as the maximum number of MTZ's per second. For a given stroke width across the skin surface SS and a required MTZ density, a maximum hand speed can be calculated. The motor speed can be set to a value corresponding to the maximum hand speed for each treatment setting selectable at the user interface panel 32. Using the number of axicon segments 74 or facets and the maximum MTZ/s, a motor speed can be determined by the controller 36. Variations in hand speed may be compensated by switching laser treatment spots on and off using an algorithm implemented in software.

Each MTZ may be configured to have a width or diameter of between 30 micrometers and 300 micrometers (e.g., treatment spot size), other preferred ranges of diameters being 40 $\mu$m to 270 $\mu$m, 50 $\mu$m to 250 $\mu$m, 60 $\mu$m to 230 $\mu$m, 70 $\mu$m to 210 $\mu$m, 80 $\mu$m to 200 $\mu$m, and 100 $\mu$m to 180 $\mu$m, respectively.

In one embodiment, the treatment energies and treatment densities are set in a progression that ramps the energy upward for a plurality of settings for the treatment operational mode. For the low intensity treatment operational mode, the energy may be set at 3 milliJoules (mJ) and the treatment density may be set at 30 MTZ per square centimeter (MTZ cm$^2$) per handpiece pass. For the medium intensity treatment operational mode, the energy may be set at 7 milliJoules and the treatment density may be set at 20 MTZ per square centimeter per handpiece pass. For the high intensity treatment operational mode, the energy may be set at 9 milliJoules and the treatment density may be set at 20 MTZ per square centimeter per handpiece pass.

From these representative values of the different settings for the treatment operational modes, the required pulse duration for the laser 16 may be calculated for each operational mode (for example, 2.5 milliseconds for low intensity, 5.8 milliseconds for medium intensity, and 7.5 seconds for high intensity). Furthermore, a maximum number of MTZ per second and maximum hand speed for each operational mode may also be calculated (for example, maximum speed of 6.7 centimeters per second for low intensity, 4.3 centimeters per second for medium intensity, and 3.3 centimeters per second for high intensity). Likewise, a default motor speed in revolutions per minute for the motor 50 may also be calculated (for example, 1091 rpm for low intensity, 468 rpm for medium intensity, and 364 rpm for high intensity). Thus, the initial operational parameters provide a starting point for the real time adjustment of the handheld apparatus 10 during a dermatological treatment.

It will be understood that other treatment densities may be used, including but not limited to treatment densities below 80 MTZ cm$^{-2}$ per handpiece pass, below 70 MTZ cm$^{-2}$ per handpiece pass, below 60 MTZ cm$^{-2}$ per handpiece pass, below 50 MTZ cm$^{-2}$ per handpiece pass, below 40 MTZ cm$^{-2}$ per handpiece pass, below 30 MTZ cm$^{-2}$ per handpiece pass, and below 20 MTZ cm$^{-2}$ per handpiece pass, while the treatment densities can be above either 0 MTZ cm$^{-2}$, 5 MTZ cm$^{-2}$, 10 MTZ cm$^{-2}$, 15 MTZ cm$^{-2}$ and 20 MTZ cm$^{-2}$. Any one of a variety of treatment energies may be used in alternative embodiments; preferred energy ranges being 0 mJ-15 mJ, 0 mJ-12 mJ, 0 mJ-10 mJ, 0.5 mJ-10 mJ, 1 mJ-10 mJ, 2 mJ-10 mJ, and 3 mJ-9 mJ, respectively. According to a preferred embodiment, with energies of 3 mJ, 7 mJ, and 9 mJ and treatment densities of 30 MTZ cm$^{-2}$, 20 MTZ cm$^{-2}$, and 20 MTZ cm$^{-2}$ per pass respectively as discussed above, the optical beam preferably is focused so as to form an optical spot size on the skin surface having a diameter between 100 $\mu$m and 180 $\mu$m, optimally 140 $\mu$m. Such spot sizes would create lesion treatment zones having diameters of approximately 97 $\mu$m, 170 $\mu$m, and 192 $\mu$m for treatment energies corresponding to 3 mJ, 7 mJ, and 9 mJ, respectively, according to one preferred embodiment of the invention.

Any combination of the above aforementioned ranges of treatment spot sizes, treatment energies, and treatment densities can be used according to the embodiments of the invention.

In one embodiment, the controller 36 is programmed and the lens L3 is configured and shaped to ensure that a fractional coverage is between 10-40 pulses/cm$^2$ per pass, a spot size of each of the pulses at the skin surface is between 80 $\mu$m and 200 $\mu$m, and an energy of each of the pulses is between 0.5 mJ and 10 mJ.

In operation, the consumer actuates the power button 38 on the user interface panel 32. The indicator ring 38a at the power button 38 lights up solid green, which indicates that the handheld apparatus 10 is powered on and no operational faults have been detected. The battery indicator light 44 also actuates to illustrate the amount of charge remaining in the internal battery 46. The handheld apparatus 10 then moves from a standby state to a ready state by actuating the operational state indicator light 42 for low intensity treatment to blink for two seconds before staying solid. The mouse LED assembly 78 then lights up, which visibly illuminates the translucent tip 26 and indicates to the consumer that movement detection has begun and the handheld apparatus 10 is in a ready state. If the operational mode selection button 40 is actuated while the handheld apparatus 10 is in the standby or ready states, the controller 36 sends updated operational parameters to the laser 16, the motor 50, and the movement/velocity detection system via the laser control 102, the motor control 100, and the mouse interface 112, respectively. The controller 36 also instructs the user interface control 98 to actuate the respective operational state indicator light 42 corresponding to the new operational mode to blink for two seconds and then stay solid. Thus, the consumer knows what operational mode the handheld apparatus 10 is in prior to the beginning of a dermatological treatment.

After the handheld apparatus 10 has entered the ready state, if no activity is detected by the user interface control 98 or the mouse detector 82 for two minutes, the mouse LED assembly 78 is deactivated by the mouse interface 112 and the controller 36 automatically returns to the default operational mode (low intensity treatment) in a standby state. If no activity continues to be detected by the user interface control 98 or the mouse detector 82 for five minutes, the controller 36 automatically shuts down the handheld apparatus 10, and the indicator ring 38a shuts off. The controller 36 also shuts down the handheld apparatus 10 if the power button 38 is actuated in the standby or ready states. In any event, the battery indicator light 44 shuts down about four seconds after the indicator ring 38a shuts off.

As described above, the controller 36 in the ready state actuates the movement/velocity detection system and continually receives movement information from the mouse detector 82. If the velocity of the tip 26 is determined to be within the desired range (e.g., above zero and above a minimum hand speed and below the maximum hand speed for the current operational mode), the controller 36 sends electrical signals actuating the laser 16 and the motor 50 to thereby enter an active dose delivery state. If at any point during the treatment, the velocity of the tip 26 changes to a value below or above the desired range, the indicator ring 38a turns off and the speaker 96 is actuated to emit a tone to indicate that the hand speed is incorrect. If no velocity or a velocity in the opposite or wrong direction of the tip 26 is detected, such as during repositioning of the handheld apparatus 10, the indicator ring 38a turns off and no sound is emitted. Once the mouse detector 82 detects further movements of the tip 26, dose delivery continues.

The laser control 102 may be configured to include a laser pulse limiter 122 that automatically stops the laser diode 64 after continuously emission of a pulse of light for a given time period. The laser control 102 also monitors every actuation of the laser diode 64 and maintains a dose counter representing the total accumulated number of pulses delivered during the current dermatological treatment. The controller 36 includes in memory a threshold number of pulses for the dermatological treatment. Once the dose counter exceeds this threshold number of pulses, the controller 36 sends a signal to the laser control 102 to shut down the laser 16 and also a signal to the audio driver 116 to actuate the speaker 96 to emit a sound indicating the completion of a treatment cycle. A visual indication at the tip 26 or the user interface panel 32 may also accompany the sound from the speaker 96. The controller 36 then enters a treatment paused state while the dose counter of the laser control 102 is reset.

During delivery of the doses, the motor control 100 and the laser control 102 are synchronized by the controller 36 with the interruptor interface 110. The software of the controller 36 is configured to monitor and maintain the speed of the motor 50 and thus the rotational speed of the rotatable component 72. As described above, the rotatable component 72 includes a number of fins 72a that interrupt detection of the source LED 68 by the interruptor detector 70. Consequently, the interruptor detector 70 sends a signal to the controller 36 that may be converted into an actual motor speed. The controller 36 can instruct the motor control 100 to increase or decrease the speed of the motor 50 if the detected actual motor speed does not correlate with the desired motor speed for the current operational mode. The rise and fall of the signal sent by the interruptor detector 70 to the controller 36 may also simultaneously be used to send signals instructing the laser control 102 when the laser diode 64 should be actuated.

To this end, each rise and fall of the signal sent by the interruptor detector 70 may cause the controller 36 to enter an Interrupt Service Routine. In each Interrupt Service Routine, the speed of the tip 26 is calculated, the motor control 100 corrects the speed of the motor 50, the laser control 102 determines when to actuate the laser diode 64 to reflect off a specific axicon segment 74, and any visual or audible feedback signals are provided at the user interface control 98. In one example, the signal rise of the interruptor detector 70 actuates a first Interruptor Service Routine wherein the speed of the tip 26 is determined from the mouse detector 82. The laser control 102 then determines when the laser diode 64 should be activated as described in further detail below. The laser 16 then fires and movement detection continues until the signal fall of the interruptor detector 70 actuates a second Interruptor Service Routine. In the second Interruptor Service Routine, the user interface control 98 actuates any necessary visual or audible feedback and then movement detection by the mouse detector 82 continues after the laser 16 stops firing. The next signal rise of the interruptor detector 70 then restarts this cycle, which continues throughout the dose delivery. It will be appreciated that only one interruptor service routine may be actuated for each rise and fall of the signal from the interruptor detector 70 in other embodiments.

The laser control 102 determines when the laser diode 64 should be actuated to ensure that a specific axicon segment 74 reflects the optical beam generated as follows. The motor 50 rotates the rotatable component 72 at the speed corresponding to the maximum firing speed of the laser 16 and the corresponding maximum velocity of the tip 26. The laser control 102 is programmed with a specific number of "gears" corresponding to a fixed number of velocity ranges within the desired range. For example, the desired range of tip velocities may be divided into 23 segments and the "gear" of the laser control 102 indicates how many axicon segments 74 out of 23 eligible axicon segments 74 are fired upon by the laser diode 64. Thus, if the detected velocity of the tip 26 by the mouse detector 82 corresponds to the tenth "gear" of the laser control 102, the laser control 102 will actuate the laser diode 64 only ten times out of every 23 eligible axicon segments 74 that pass by the laser 16. It will be understood that the fractional pattern of microscopic treatment zones are effectively randomized by the laser control 102 by selecting a number of "gears" for the laser control 102 that does not share a divisor with the number of axicon segments 74 on the rotatable component 72 (and hence, this is another reason odd or prime numbers of axicon segments 74 are typically chosen for the optical pattern generator 14). It will also be understood that the 23 "eligible" axicon segments 74 that the laser 16 may fire upon in a cycle may correspond to every other or every third axicon segment 74 that rotates past the laser diode 64 such that the laser 16 does not fire on consecutive axicon segments 74 during rotation of the rotatable component 72. Alternatively, the "eligible" axicon segments 74 that the laser 16 may fire upon in a cycle may correspond to one or more consecutive axicon segments 74 during rotation of the rotatable component 72, it being understood that it is preferred that at least one or more axicon segments not be fired each rotation of the rotatable component (or each completion of a gear cycle) to facilitate a more randomized skin treatment. However, firing each and every axicon segment in the highest gear is one preferred embodiment of the invention.

Further disclosure on pulse drop algorithms that may be employed in the apparatus 10 may be found in U.S. Pat. No. 7,824,395, which is hereby incorporated by reference herein in its entirety.

The controller 36 may provide a feed forward signal to the consumer to alert the consumer of an operational variable of the apparatus yet to be adjusted. The controller 36 may also provide a feed forward signal to the consumer such that the consumer is alerted to and understands the fault or problem preventing operation of the handheld apparatus 10. The signal may be a visual indicator that is visible from the exterior of the outer housing 12 and that is readily perceivable to the consumer. The visual indicator may be visible light of periodically-variable intensity that generates a blinking pattern, which may mimic a rhythm of breathing, and may originate from the mouse LED assembly 78, the indicator ring 38a, or one of the other indicator lights on the user interface panel 32.

As described above, the controller 36 is prevented from powering the laser 16 in response to the tip 26 not being engaged with the outer housing 12. As explained above, the tip detector 58 is a Hall Effect sensor that sends a signal via the Hall receiver 108 to the controller 36 to indicate whether a tip 26 is on the handheld apparatus 10. If the tip 26 is not currently detected by the tip detector 58, the controller 36 may actuate the user interface control 98 or the mouse LED assembly 78 to provide a visual indicator indicating that the error is a missing tip 26. In one example, the mouse LED assembly 78 (which is normally actuated to be solid during the ready state of the controller 36 such that movement detection is enabled) may be actuated by electrical pulses from the mouse interface 112 to blink with a periodically-variable intensity. The driving circuit of the mouse LED assembly 78 communicates electrical pulses to the visual indicator to generate light with the periodically-variable intensity. The periodically-variable intensity of the mouse LED assembly 78 may provide a blinking pattern, which may mimic a rhythm of breathing, and the noticeable blinking or flashing of the LED adjacent the missing tip 26 will indicate to the consumer that the tip 26 is missing. Alternatively, the indicator ring 38a may be activated to blink with a red color or a green color to indicate the missing tip 26.

In another example, if the charge of the internal battery 46 drops below an operational level during any of the standby, ready, or dose delivery states of the controller 36, the user interface control 98 may be actuated to blink the battery indicator light 44 orange for four seconds before shutting the handheld apparatus 10 down. Thus, a consumer will immediately understand that the internal battery 46 must be recharged. If the temperature of the laser 16 or the outer housing 12 sensed by the temperature sensor 54 exceeds the predetermined temperature threshold, the controller 36 may send a signal to the fan control 104 to keep the fan 56 operating while also sending a signal to the user interface control 98 to actuate the indicator ring 38a to blink red until the temperature returns to a value below the threshold. Once the temperature returns to a tolerable level below the threshold, the power indicator ring 38a is actuated to become solid green and the laser 16 may be actuated again. For any other fault detected by the controller 36, the user interface control 98 may be actuated to light the indicator ring 38a solid red and all other functions of the handheld apparatus 10 may be deactivated until the fault is repaired or corrected. Thus, the software of the controller 36 is configured to communicate with the consumer when any fault preventing normal operation occurs.

The handheld apparatus 10, which is configured for use by a non-physician consumer for fractionally resurfacing skin of the consumer, may include a visual indicator supported by the outer housing 12 and the visual indicator may configured to generate light that is perceivable from the exterior of the outer housing 12. A driving circuit (not shown), which is also inside the outer housing 12, is operatively coupled to the controller 36. The driving circuit is configured to communicate electrical pulses to the visual indicator that generate the light with a periodically-variable intensity to create a blinking pattern. The blinking pattern provides a feed forward signal for the consumer to alert the consumer of an operational variable of the handheld apparatus 10 yet to be adjusted When the charging control 94 detects that the power supply 84 is coupled to an power adapter 90 or the charging/storage base 92, the charging control 94 sends a signal to the controller 36 that indicates the handheld apparatus 10 is in a charging state. The charging control 94 also causes power (i.e., direct current (DC) power) to be supplied from the power adapter 90 to the controller 36 and the battery 46 and monitors the amount of charge remaining in the battery 46. The controller 36 receives the charging signal including the amount of charge in the battery 46 and sends an electrical signal to the user interface control 98, which actuates the battery indicator light 44 to light up and illustrate the current amount of charge in the internal battery 46. Once the battery has been recharged, the consumer may remove the handheld apparatus 10 from the charging/storage base 92, which causes the charging control 94 to send a signal indicating the disconnection to the controller 36. The controller 36 then actuates the user interface control 98 to shut off the battery indicator light 44 after four seconds following the disconnection from the charging/storage base 92.

In summary, the handheld apparatus 10 may be used by a consumer to perform a dermatological treatment, such as fractional skin resurfacing. During treatment, the consumer moves the tip 26 of the handheld apparatus 10 over a treatment area of the skin surface SS. Pulses from the laser 16 are deflected by the optical pattern generator 14 into the skin surface SS to form a plurality of microscopic treatment zones (MTZs) dispersed among and surrounded by non-treated areas of minimally-damaged or undamaged tissue. The velocity of the tip 26 is detected by the mouse detector 82, and the laser 16 is controlled according to this detected velocity. Consequently, a generally constant amount of energy per unit of skin surface SS is deposited regardless of velocity variations during treatment. The tip 26 includes integrated rollers 30 and is configured to be easily removed from the outer housing 12 for cleaning after a dermatological treatment. The handheld apparatus 10 provides visual and/or audible feedback before, during, and after treatment to enable the consumer to reliably use the handheld apparatus 10 in a home setting for treating the consumer's skin.

An optical tracking gel may be applied to the skin surface SS prior to the skin resurfacing dermatological treatment. The optical tracking gel optimizes the velocity detection of the mouse detector 82 and thus the control of the laser 16. The optical tracking device, which is provided by the movement/velocity detection system comprised of the mouse LED assembly 78, the mouse imaging optics 80, and the mouse detector 82, illuminates the water soluble optical tracking gel to track motion of the outer housing 12.

The apparatus 10 is intended to be operated by a consumer in a home environment (bathroom, bedroom, living room, etc.). A typical treatment protocol may include one or more weekly treatments to produce a perceivable treatment outcome and then periodical treatments at a frequency to sustain the treatment outcome. Each individual skin area may be treated with multiple passes (e.g., four passes) during which a treatment area (e.g., cheeks, forehead, neck, chest, hands, etc.) of the skin is fractionally resurfaced. The apparatus 10 may be configured to operate while being moved in a linearly reciprocating manner in forward and backward directions, or moved in only a single direction, relative to the skin surface SS while delivering a standard amount of energy (i.e., treatment dose) corresponding to a pre-defined treatment area.

A function of apparatus 10 is to deliver laser energy of a certain wavelength, intensity, spot geometry and spot distribution to the skin. Another function of apparatus 10 is to deliver a laser spot with a certain spot geometry and power, which includes switching the laser on and off to control the energy (in mJ) and spot density (number of MTZ/cm$^2$). Another function of apparatus 10 is to move the laser spot using the motorized axicon wheel or other similar rotating element to create certain spot distribution on the skin. Yet another function of apparatus 10 is to measure handpiece speed with the mouse optics and to compensate the treatment for perceived variations in the handpiece speed. Another function is to configure the treatment by allowing the user to set treatment intensity (consisting of pulse energy and MTZ density) with buttons or other controls at the user interface. Another function is to provide user feedback with the user interface LED's and/or speaker on guiding the handpiece, feedback on speed, feedback showing system state, etc.

Product documentation may be supplied with the handheld apparatus 10 and may include an instruction manual that provides the consumer with written use instructions and illustrations and/or images to supplement the written text. The consumer may also be supplied with an instruction movie distributed on a CD, a DVD, or a flash memory data storage device such as a USB flash drive, as well as a quick start card to guide the user during initial operation after the handheld apparatus 10 is removed from its consumer packaging.

The apparatus is configured to provide low power level, repeat fractional treatments that are suitable for a non-physician consumer who is self-administering the treatments in a home setting. The treatments may be repeated at frequent intervals, i.e. daily, or even several times a day, weekly, monthly or at other appropriate intervals.

References herein to terms such as "vertical", "horizontal", etc. are made by way of example, and not by way of limitation, to establish a frame of reference. Terms, such as "on", "above", "below", "side", "upper", "lower", "over", "beneath", and "under", are defined with respect to a horizontal plane. It is understood that various other frames of reference may be employed for describing the invention without departing from the spirit and scope of the invention. It is also understood that features of the invention are not necessarily shown to scale in the drawings.

It will be understood that when an element is described as being "attached", "connected", or "coupled" to or with another element, it can be directly connected or coupled to the other element or, instead, one or more intervening elements may be present. In contrast, when an element is described as being "directly attached", "directly connected", or "directly coupled" to another element, there are no intervening elements present. When an element is described as being "indirectly attached", "indirectly connected", or "indirectly coupled" to another element, there is at least one intervening element present.

It will be understood that when an element as a layer, region or substrate is described as being "on" or "over" another element, it can be directly on or over the other element or intervening elements may also be present. In contrast, when an element is described as being "directly on" or "directly over" another element, there are no intervening elements present. It is also understood that features of the present invention are not necessarily shown to scale in the drawings.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "composed of", "includes", "having", "has", "with", or variants thereof are used in either the detailed description or the claims, such terms are intended to be inclusive in a manner similar to the term "comprising."

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described.

What is claimed is:

1. A handheld apparatus for use by a non-physician consumer for fractionally resurfacing skin of the consumer, comprising:

a housing dimensioned to be manually grasped and manipulated relative to a skin surface of the consumer;

a laser inside the housing, the laser configured to generate an optical beam containing coherent electromagnetic radiation;

an optical pattern generator inside the housing, the optical pattern generator including a rotatable component that continually rotates during operation of the laser about a rotation axis in a single direction, thereby deflecting the optical beam during rotation to divide the electromagnetic radiation into pulses that propagate from the housing toward the skin surface and form a fractional pattern at the skin surface for performing a skin resurfacing dermatological treatment, the rotatable component including a plurality of fins and a corresponding plurality of reflective segments that rotate through the optical beam to deflect and divide the optical beam into the pulses;

a transducer configured to output a signal for each pulse of the electromagnetic radiation generated by the rotatable component, the transducer including an encoder having a source light and a detector positioned within the housing such that one of the plurality of fins rotates to interrupt a path between the source light and the detector each time one of the pulses is generated by the rotatable component; and a controller inside the housing and operatively coupled to the transducer, the controller working during operation of the laser to determine an accumulated number of pulses by counting each signal communicated from the transducer, and to compare the accumulated number of pulses with a threshold number of pulses associated with the end of a dose of radiation.

2. The handheld apparatus of claim 1 further comprising:

a power source disposed inside the housing, the power source configured to supply electrical power to the laser and the rotatable component to perform the skin resurfacing dermatological treatment without requiring connection to an external power source during the skin resurfacing dermatological treatment.

3. The handheld apparatus of claim 2 wherein the power source is a rechargeable battery.

4. The handheld apparatus of claim 1 wherein the plurality of reflective segments on the rotatable component of the optical pattern generator includes a plurality of reflective axicon segments, and the rotatable component is positioned relative to the laser so that the reflective axicon segments rotate through the optical beam as the rotatable component rotates about the rotation axis.

5. The handheld apparatus of claim 4 wherein at least two of the reflective axicon segments are configured to deflect the optical beam by different angular deflections.

6. The handheld apparatus of claim 1 wherein the rotatable component of the optical pattern generator includes a spinning wheel with a plurality of deflection sectors arranged around the rotation axis, each of the deflection sectors including at least two reflective surfaces that in combination deflect the optical beam by a substantially constant angular deflection as each of the deflection sectors rotates through the optical beam.

7. The handheld apparatus of claim 6 wherein at least two of the deflection sectors are configured to deflect the optical beam by different angular deflections.

8. The handheld apparatus of claim 1 wherein the controller is operatively coupled with the laser and the optical pattern generator for controlling operation of the laser and the rotatable component to form the pulses of the electromagnetic radiation.

9. The handheld apparatus of claim 1 wherein the laser is configured to generate the coherent electromagnetic radiation in the optical beam at a wavelength between 1.42 µm and 1.45 µm.

10. The handheld apparatus of claim 1 further comprising:
a plurality of rollers coupled with the housing, the rollers configured to contact the skin surface as the housing is manually manipulated relative to the skin surface and to provide a massaging effect that reduces pain sensations during the skin resurfacing dermatological treatment so as to not require use of an anesthetic during the skin resurfacing dermatological treatment.

11. The handheld apparatus of claim 1 further comprising:
a converging lens disposed in an optical path for the optical beam after deflection by the rotatable component of the optical pattern generator, the converging lens having a focal point above the skin surface.

12. The handheld apparatus of claim 11 wherein the focal point is inside the housing.

13. The handheld apparatus of claim 11 wherein the converging lens comprises a simple lens.

14. The handheld apparatus of claim 11 wherein the converging lens is an element of a compound lens.

15. The handheld apparatus of claim 1 wherein the laser is a laser diode.

16. The handheld apparatus of claim 1 further comprising:
an indicator configured to produce either a visual or audible end of dose indication for the consumer, the indicator being operatively coupled to the controller such that the controller causes the indicator to activate to produce the visual or audible end of dose indication if the accumulated number of pulses exceeds the threshold number of pulses.

17. The handheld apparatus of claim 1, wherein a water soluble optical tracking gel is configured to be applied to the skin surface prior to the skin resurfacing dermatological treatment, and the handheld apparatus further comprises:
an optical tracking device which illuminates the water soluble optical tracking gel to track motion of the housing accurately during operation of the laser.

18. The handheld apparatus of claim 1, wherein the plurality of reflective segments each deflect the optical beam by differing angles, and a number of the reflective segments is a prime number.

19. The handheld apparatus of claim 1, further comprising:
a rechargeable battery inside the housing; and
a fan inside the housing, the housing and the fan being constructed and configured to cause outside air to be blown through the housing and transfer heat way from the laser so that at least some of the heat is transferred to the rechargeable battery causing the rechargeable battery to be heated.

* * * * *